United States Patent
Krebs et al.

(10) Patent No.: US 9,745,353 B2
(45) Date of Patent: Aug. 29, 2017

(54) PRODUCTION OF ANTI-PEPTIDE ANTIBODIES

(75) Inventors: Joseph Krebs, Austin, TX (US); Paul Morrison, Austin, TX (US); Jun Wang, Austin, TX (US)

(73) Assignee: Bioo Scientific Corporation, Austin, TX (US)

( * ) Notice: Subject to any disclaimer, the term of this patent is extended or adjusted under 35 U.S.C. 154(b) by 251 days.

(21) Appl. No.: 13/990,344

(22) PCT Filed: Nov. 29, 2011

(86) PCT No.: PCT/US2011/062318
§ 371 (c)(1),
(2), (4) Date: Oct. 18, 2013

(87) PCT Pub. No.: WO2012/074966
PCT Pub. Date: Jun. 7, 2012

(65) Prior Publication Data
US 2014/0046035 A1    Feb. 13, 2014

Related U.S. Application Data

(60) Provisional application No. 61/417,653, filed on Nov. 29, 2010.

(51) Int. Cl.
| | | |
|---|---|---|
| *C07K 14/195* | (2006.01) | |
| *C07K 16/00* | (2006.01) | |
| *A61K 39/00* | (2006.01) | |
| *C07K 19/00* | (2006.01) | |
| *C07K 16/40* | (2006.01) | |
| *C12N 9/02* | (2006.01) | |

(52) U.S. Cl.
CPC ............ *C07K 14/195* (2013.01); *C07K 16/00* (2013.01); *C07K 16/40* (2013.01); *C12N 9/0008* (2013.01); *A61K 2039/6031* (2013.01); *A61K 2039/6043* (2013.01); *C07K 2319/00* (2013.01)

(58) Field of Classification Search
None
See application file for complete search history.

(56) References Cited

U.S. PATENT DOCUMENTS

| 5,243,038 A * | 9/1993 | Ferrari .......... C07K 14/43586 435/320.1 |
| 2002/0044951 A1* | 4/2002 | Liu .................. A61K 31/661 424/264.1 |
| 2002/0045567 A1* | 4/2002 | Cappello .......... A61L 17/10 514/17.2 |
| 2005/0208628 A1* | 9/2005 | Duan ................ C07K 14/005 435/70.21 |

FOREIGN PATENT DOCUMENTS

PT    WO 2007105169 A2 *   9/2007 .......... A61K 39/092

OTHER PUBLICATIONS

Zhou et al. "A novel multivalent vaccine based on secretary antigen-delviery induces protective immunity against Vibrio anguillarum and Aeromonas hydrophila" J. Biotechnology 146 (2010) 25-30.*
Ilyinskii et al. "Adjuvant potential of aggregate-forming polyglutamine domains" Vaccine vol. 26(26), pp. 3223-3226 (Apr. 18, 2008).
Shamji et al. "Development and characterization of a fusion protein between thermally responsive elastin-like polypeptide and interleukin-1 receptor antagonist: sustained release of a local antiinflammatory therapeutic" Arthritis and Rheumatism. vol. 56(11), pp. 3650-3661 (Nov. 2007).
Floss et al. "Expression and immunogenicity of the mycobacterial Ag85B/ESAT-6 antigens produced in transgenic plants by elastin-like peptide fusion strategy" Journal of Biomedicine and Biotechnology. vol. 2010, ID.274346 (Apr. 13, 2010).
Jain et al. "Accelerated stability studies for moisture-induced aggregation of tetanus toxoid" Pharmaceutical Research. vol. 28(3), pp. 626-639 (Nov. 12, 2010).
International Search Report/Written Opinion for PCT Application No. PCT/US2011/062318 issued Aug. 31, 2012.
International Preliminary Report on Patentability for PCT Application No. PCT/US2011/062318 issued Jun. 4, 2013.

* cited by examiner

*Primary Examiner* — Daniel E Kolker
*Assistant Examiner* — James Rogers
(74) *Attorney, Agent, or Firm* — Meyertons, Hood, Kivlin, Kowert & Goetzel, P.C.

(57) ABSTRACT

Anti-peptide antibodies (APAs) are extremely important tools for biomedical research. Many important techniques, such as immunoblots, ELISA immunoassays, immunocytochemistry, and protein microarrays are intrinsically linked to APA function and completely dependent on APA quality. Unfortunately, not all commercially-available APAs have good antigen binding characteristics; as a result, researchers are often unable to perform high quality protein analysis experiments. This disclosure describes a new method for the scalable production of polyclonal APAs using recombinant antigens. These recombinant peptide antigens have several advantages over traditional peptide antigens which improve the ease and speed of antibody production. The recombinant antigens can be scalably produced and purified much faster than traditional synthetic peptide-conjugates. These recombinant antigen-carriers are designed to specifically aggregate in vivo after administration into the host; this aggregation greatly enhances immunogenicity and may eliminate the need for the use of chemical adjuvants which cause physical irritation and discomfort to the host.

10 Claims, 4 Drawing Sheets

SEQUENCE LISTING

<160> NUMBER OF SEQ ID NOS: 4

<210> SEQ ID NO 1
<211> LENGTH: 812
<212> TYPE: PRT
<213> ORGANISM: Artificial Sequence
<220> FEATURE:
<223> OTHER INFORMATION: Synthetic Sequence

<400> SEQUENCE: 1

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg

-continued

```
            355                 360                 365
Val Ala Lys Leu Ala Gly Gly Val Ala Val Ile Lys Val Gly Ala Ala
            370                 375                 380
Thr Glu Val Glu Met Lys Glu Lys Lys Ala Arg Val Glu Asp Ala Leu
385                 390                 395                 400
His Ala Thr Arg Ala Ala Val Glu Glu Gly Val Val Ala Gly Gly Gly
                    405                 410                 415
Val Ala Leu Ile Arg Val Ala Ser Lys Leu Ala Asp Leu Arg Gly Gln
            420                 425                 430
Asn Glu Asp Gln Asn Val Gly Ile Lys Val Ala Leu Arg Ala Met Glu
            435                 440                 445
Ala Pro Leu Arg Gln Ile Val Leu Asn Cys Gly Glu Glu Pro Ser Val
            450                 455                 460
Val Ala Asn Thr Val Lys Gly Gly Asp Gly Asn Tyr Gly Tyr Asn Ala
465                 470                 475                 480
Ala Thr Glu Glu Tyr Gly Asn Met Ile Asp Met Gly Ile Leu Asp Pro
                    485                 490                 495
Thr Lys Val Thr Arg Ser Ala Leu Gln Tyr Ala Ala Ser Val Ala Gly
            500                 505                 510
Leu Met Ile Thr Thr Glu Cys Met Val Thr Asp Leu Pro Lys Asn Asp
            515                 520                 525
Ala Ala Asp Leu Gly Ala Ala Gly Gly Met Gly Gly Met Gly Gly Met
            530                 535                 540
Gly Gly Met Met Leu Glu Glu Leu Gly Pro Gly Val Gly Val Pro Gly
545                 550                 555                 560
Val Gly Val Pro Gly Leu Gly Val Pro Gly Val Gly Val Pro Gly Leu
                    565                 570                 575
Gly Val Pro Gly Val Gly Val Pro Gly Leu Gly Val Pro Gly Val Gly
            580                 585                 590
Val Pro Gly Leu Gly Val Pro Gly Val Gly Val Pro Gly Leu Gly Val
            595                 600                 605
Pro Gly Val Gly Val Pro Gly Leu Gly Val Pro Gly Val Gly Val Pro
610                 615                 620
Gly Leu Gly Val Pro Gly Val Gly Val Pro Gly Leu Gly Val Pro Gly
625                 630                 635                 640
Val Gly Val Pro Gly Val Gly Val Pro Gly Leu Gly Val Pro Gly Val
                    645                 650                 655
Gly Val Pro Gly Leu Gly Val Pro Gly Val Gly Val Pro Gly Leu Gly
            660                 665                 670
Val Pro Gly Val Gly Val Pro Gly Leu Gly Val Pro Gly Val Gly Val
            675                 680                 685
Pro Gly Leu Gly Val Pro Gly Val Gly Val Pro Gly Leu Gly Val Pro
            690                 695                 700
Gly Val Gly Val Pro Gly Leu Gly Val Pro Gly Val Gly Val Pro Gly
705                 710                 715                 720
Leu Gly Val Pro Gly Val Gly Val Pro Gly Val Gly Val Pro Gly Leu
                    725                 730                 735
Gly Val Pro Gly Val Gly Val Pro Gly Leu Gly Val Pro Gly Val Gly
            740                 745                 750
Val Pro Gly Leu Gly Val Pro Gly Val Gly Val Pro Gly Leu Gly Val
            755                 760                 765
Pro Gly Val Gly Val Pro Gly Leu Gly Val Pro Gly Val Gly Val Pro
            770                 775                 780
```

```
Gly Leu Gly Val Pro Gly Val Gly Val Pro Gly Leu Gly Val Pro Gly
785                 790                 795                 800

Val Gly Val Pro Gly Leu Gly Val Pro Gly Trp Pro
                805                 810

<210> SEQ ID NO 2
<211> LENGTH: 5
<212> TYPE: PRT
<213> ORGANISM: Artificial Sequence
<220> FEATURE:
<223> OTHER INFORMATION: Synthtic Sequence

<400> SEQUENCE: 2

Val Pro Gly Val Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 3

Val Pro Gly Phe Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 4

Val Pro Gly Xaa Gly
1               5
```

PRODUCTION OF ANTI-PEPTIDE ANTIBODIES

STATEMENT REGARDING FEDERALLY SPONSORED RESEARCH OR DEVELOPMENT

This invention was made with government support under NIH SBIR grant 1R43AI072858-01. The government has certain rights in the invention.

FIELD OF THE INVENTION

The present invention relates to the production of antibodies produced to bind antigens such as peptide or protein targets.

DESCRIPTION OF THE RELEVANT ART

Antibodies are valuable reagents for biomedical research. Their unparalleled, exquisite specificity and sensitivity enable the binding of specific ligands in biological systems with high selectivity. Consequently, a number of antibody-based analytical techniques have been developed through the years to detect biomolecules such as Western blots (immunoblots), ELISA (enzyme-linked immunosorption assay), protein microarrays and immunocytochemistry-based detection. Antibody-based techniques have also been developed to detect and/or purify specific cell types in cell mixtures such as immunohistochemistry and FACS (fluorescence-assisted cell sorting). Antibodies are also used to purify biomolecules from cell extracts via immunoprecipitation or by immobilization to solid supports such as Protein A conjugated beads.

Antibodies produced by immunizing hosts with a peptide antigen are known as anti-peptide antibodies (APAs). If the peptide antigen sequence was derived from a protein, then the antibodies can often recognize and bind the source protein itself. For this reason, many (APAs) are protein-specific, anti-protein antibodies. These antibodies are extremely valuable and useful for the detection, characterization and purification of proteins in complex mixtures. APAs are able to distinguish between proteins possessing highly similar primary sequences and post-translational modifications which are impossible to distinguish by any other known analytical method. This is a highly beneficial trait since biological mixtures often contain many homologous proteins which possess subtle yet important structural differences, such as point mutations and specific post-translational modifications such as phosphorylation. APAs can even recognize conformational changes in proteins, such as the disease causing structural changes occurring in prion proteins. APAs can also inhibit specific proteins and enzymes in vitro or when injected into cells and can be used to study the subcellular location of a protein or epitope. In many cases, APAs are the best means to cost-effectively detect and purify specific components of the proteome. Antibody-based approaches have been used to clone tissue specific proteins, construct protein microarrays, and biosensors and profile global protein expression in normal versus cancerous tissues. Unfortunately the quality of commercial APAs is frequently poor which prevents researchers from performing these techniques with optimal sensitivity. Consequently, to perform the desired testing, researchers must either make the antibody themselves or have it made by a custom service provider; this process takes several months.

New antibodies are produced through an immune response by immunizing a host organism with a target antigen. Unfortunately not all types of target molecules are good antigens for antibody production; this is especially true for peptide antigens used to make anti-peptide and anti-protein antibodies. A large proportion of the current antibody manufacturing process is focused on increasing the antigenicity/immunogenicity of the target antigens. Unfortunately, this process is often unsuccessful generating the desired, high quality antibodies, so APAs frequently lack the avidity and specificity required for commonly used research applications. As a consequence, the ability of researchers to use antibody-based techniques to their full potential is critically limited by both the availability and the quality of the antibody reagents. Improvements in the manufacturing process of anti-peptide antibodies would hTR to eliminate this bottleneck.

Polyclonal APAs are produced in a multi-step process which takes several months to complete start to finish:

i) The first step is the design of peptide antigens for immunization. A number of computer-based methods are available to aid peptide antigen design; these methods analyze a number of physical and sequence parameters to select optimal antigen sequences. Nevertheless, antigen design is still somewhat empirical; it is useful to design, produce and test multiple peptide sequences to increase the chances for success.

ii) After the antigen sequence has been designed, it is synthesized by solid-phase peptide synthesis. The addition of each amino acid residue requires multiple chemical reaction steps. Detrimental side reactions occur at each step, especially when certain amino acids are present in the sequence. After addition of the last residue, the peptide side chains are deprotected and the peptide is liberated from the solid support.

iii) After synthesis, the deprotected peptide is purified using high-performance liquid chromatography (although other simpler purification methods are sometimes used, higher levels of impurities remain after purification). Since peptides possess widely varying physical properties, the purification procedure cannot be standardized; each peptide is purified individually. For longer peptides (>10 residues), the product usually contains significant levels of impurities—these impurities are often closely related to the desired product and are very difficult to separate from the desired peptide antigen.

iv) Since peptides are usually not immunogenic, they are coupled to a large protein called a carrier immunogen. The coupling of the antigen to the immunogen is performed via functional groups on the peptide and immunogen. Since it is undesirable to modify the structure of the antigen, extra amino acid residues are sometimes added to the peptide to facilitate coupling. Nevertheless, the coupling reactions can sometimes affect the structure of the peptide antigen.

v) The peptide-immunogen conjugate is then mixed with an adjuvant and injected into the host (usually in more than one animal since immune response between animals can vary). The injections are repeated every two weeks for about 3 months. The first injection uses "complete" adjuvant containing killed mycobacteria to create a stronger immune response; subsequent "booster" immunizations lack mycobacteria.

vi) After the initial immunization (and subsequent booster immunizations), blood is periodically collected from the hosts, processed to make serum, and analyzed to measure both the antibody titer and specificity using ELISA or Western blot techniques. When a high titer is observed, a larger quantity of blood is collected and processed to make serum.

vii) Finally, to remove serum proteins, the antibodies are sometimes purified using a solid support such as immobilized Protein A. If purified antigen-specific antibodies are required, the peptide antigen is chemically coupled at a solid support. The resulting immunoaffinity matrix can be used to purify the peptide-specific antibodies from other antibodies.

While this production method works sufficiently in many cases, it is very slow, labor intensive and requires the synthesis, purification and conjugation of diverse peptides. The diverse chemical nature of peptides makes the development of universal methodologies for antigen production extremely difficult; this consequence in turn severely limits the throughput of antibody production. High-throughput production of quality antibodies is clearly incompatible with the current production methods and requires new method development.

The immunogenicity of biomolecules is associated with the size of the antigen. Small peptides are usually poor antigens that present limited antigenic determinants to the host immune system; in contrast, larger peptides and proteins provide multiple antigenic determinants to elicit a stronger antibody response. By coupling peptide antigens to larger, foreign proteins, their antigenicity is increased dramatically. For this reason, peptide antigens for antibody production are usually prepared by chemically coupling a synthetic peptide antigen to a larger antigenic carrier protein. The best known carrier protein, keyhole limpet hemocyanin (KLH) in particular is prone to aggregation; this aggregation behavior is an important feature that makes KLH a very strong carrier immunogen for commercial antibody production. While KLH is a very good immunogen, it possesses limited solubility and is prone to spontaneous aggregation and precipitation, making it difficult to work with before, during and after the antigen conjugation step.

Over the years, emulsion formulations of adjuvants containing oily compounds and killed bacteria (such as *mycobacterium tuberculosis*) have been developed to assist the host's immune response to target antigens. After mixing the adjuvant with the antigen, the sample is mixed vigorously for several minutes to produce a stable oil-water emulsion. When injected subcutaneously into the host, these adjuvant-antigen emulsions sequester the antigen and slowly release the antigen into the host over long periods of time. This effect, called the "depot effect," allows continual long-term exposure of the antigen in the host which can greatly enhance the immune response. In addition, the killed bacteria in complete adjuvants can also enhance the immune response by inducing macrophage aggregation at the injection site.

Bacterial expression systems (such as *E. coli*) have been embraced as platforms for recombinant peptide production. Because of recent advances such as these, the cost of producing polypeptides in bacterial systems is lower than producing them by chemical synthesis for large scale production—cost comparisons for small-scale production are becoming favorable as well. Unlike traditional chemical synthesis, production of peptide antigens using recombinant production methods will produce essentially only full length peptide.

Small peptides are conjugated to larger carrier proteins to make them more antigenic. This coupling improves antigenicity by increasing the number of (required) antigenic determinants at or near the target peptide which promote the immune response. The physical characteristics of carrier-immunogens have a strong influence on their immunogenicity. One physical characteristic of carrier immunogens is a structural dissimilarity to host proteins: immunogenic proteins often contain structural features not found in host protein molecules. Expression of carrier proteins in bacteria would be an efficient way to produce carrier immunogens, but it would also be beneficial to identify proteins containing antigenic posttranslational modifications (such as glycosylation) since such modifications would likely increase the immunogenicity of the protein. While it is often difficult to express post-translationally modified proteins in bacteria, native *E. coli* glycoproteins such as Ag43 and AIDA-I might be strong immunogens since they contain immunogenic sugar (heptose) groups which are not found in mammals.

The aggregation state of a protein also influences its immunogenicity. Good carrier proteins tend to form aggregates. These particulates are optimally presented to the host immune system, generating a strong immune response. Unfortunately the very properties of a protein which make them immunogenic also make them difficult to work with in the laboratory, since proteins prone to aggregation often precipitate from solution at inopportune times, such as during peptide coupling reactions. The tendency of carrier proteins such as KLH to aggregate diminishes their ability to be used for the robust parallel synthesis required for high-throughput antigen production. It would be highly beneficial to produce carrier proteins which exist as soluble monomers in the laboratory (to facilitate purification and conjugation to antigens), but which form beneficial immunogenic aggregates when injected into the host.

Protein engineering techniques can be used to control the biochemical and physical properties of recombinant proteins. Modification of carrier antigens using protein engineering techniques could enhance their utility as immunogens. Recent bioengineering efforts have produced peptide tags, such as thermally-responsive aggregation peptides (TRAs), which have very remarkable structural properties. When fused to recombinant target proteins, these thermally-responsive peptides cause a reversible, temperature-dependent aggregation of the entire fusion protein. At lower temperatures (usually less than 30° C. for some TRA sequences), the fusion proteins are highly soluble; when the temperature is raised only a few degrees (usually greater than 30° C., depending on the particular sequences and ionic strength), the proteins undergo a reversible phase-transition which causes them to aggregate and precipitate (FIG. 1). Peptide antigen-carrier immunogen proteins could be fused to these TRA sequences to control the solubility and aggregation of the antigen. For example, the DNA sequence encoding the thermally-responsive peptide can be subcloned into the open reading frame to produce peptide antigen-carrier fusion proteins. These modified fusion proteins would be monomeric when handled at lower temperatures in vitro prior to immunization but could spontaneously aggregate after injection into rabbits or other hosts. The aggregation would improve the immune response by increasing the size of the antigen-immunogen protein. In vivo precipitation of the aggregated fusions may also enhance the peptide immunogenicity of even further by creating a slowly dissolving particle in the host (akin to the "depot effect" caused by adjuvants described above). These aggregation/precipitation properties would make these fusion proteins ideal recombinant carrier immunogens for producing anti-peptide antibodies and permit subsequent purification of the recombinant antigen carriers during antigen production.

SUMMARY OF THE INVENTION

This disclosure describes novel reagents and processes for the production of anti-peptide and anti-protein antibodies. These reagents and processes can also be used to make vaccines to prevent the spread of infectious diseases.

A recombinant fusion protein containing a target peptide antigen fused to an immunogenic carrier protein containing a thermally-responsive aggregation (TRA) polypeptide is used to control protein aggregation. The fusion protein can be produced at high levels in bacterial expression cultures and purified using a variety of methods such column chromatography and thermal-cycling. At lower temperatures the fusion protein is soluble, easy to purify, manipulate, and inject into the host organism. At higher temperatures (above about 30 degrees ° C.), the thermally-responsive peptide moiety induces aggregation of the fusion protein. This heat-induced aggregation increases the antigenicity of the protein after it is administered into a host organism (since the body temperature of many organisms is >30 degrees ° C.); the higher antigenicity causes efficient production of specific anti-peptide antigen antibodies by the host. The antibodies produced in using this procedure can be used for a wide variety of biomedical applications. The target protein can also contain known peptide sequences which activate T cells and/or or B cells; these sequences further enhance the immune response generated by protein.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
FIG. 1 depicts an open reading frame for a recombinant peptide antigen linked to a carrier protein (GroEL) containing a thermally-responsive aggregation polypeptide. The fusion proteins can also contain sequence tags for affinity purification (such as His$_6$ tags) or B-cell and/or T-cell activating sequences to enhance immune response.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Our method uses a recombinant expression system to produce peptide antigens fused to carrier proteins containing thermally-responsive polypeptides. In one embodiment, it uses a bacterial expression plasmid containing a multiple cloning site (to insert the antigen gene) in-frame with and upstream of a DNA span encoding a recombinant carrier protein (such as GroEL protein) fused at its 3' end to a thermally responsive polypeptide (TRA). The TRA polypeptide must be of sufficient size to induce a temperature induced phase aggregation to the entire fusion protein in the range of 25-37° C.

In our invention a DNA sequence encoding target peptide antigens are produced using a gene synthesis technique such as PCR amplification using overlapping oligonucleotides. The synthetic DNA gene encoding the antigen is inserted into the plasmid multiple cloning site so that the peptide is expressed as a fusion partner with the carrier-TRA protein. This carrier protein is highly immunogenic and contains a thermally-responsive (TRA) protein segment which causes the reversible aggregation of the fusion proteins at around 37° C. (normal body temperature of warm-blooded animals such as mammals). The size and amino acid sequence of the TRA segment is designed to direct the reversible aggregation of the immunogenic carrier and peptide antigen to which it is attached. When this expression plasmid is inserted into a bacterial expression strain (such as BL21 DE3), the cells will produce a recombinant protein comprised of a peptide antigen-carrier-TRA fusion. The solubility and aggregation state of the fusion protein containing the target antigen is controlled by the thermally-responsive TRA moiety. Of course it is obvious to an individual skilled-in-the-art that the protein could also be produced in other nonbacterial expression systems for recombinant protein production such as yeast, insect cells, plants, and mammalian cell cultures. At lower temperatures (below about 25-30° C.), the antigen-carrier-TRA fusion protein is soluble while at higher temperatures (near mammalian body temperature of about 37° C.) it aggregates and may form an insoluble particle. After the protein is produced it is purified from the other cellular proteins using a protein purification technique such as column chromatography or thermal cycling. The solubility of the protein at the lower temperatures facilitates its facile purification, handling and manipulation before immunization. After purification the protein is mixed with Adjuvant (such as Freund's Adjuvant) and the resulting emulsion is used to immunize rabbits, mice, goats or other hosts for antibody production. Serum collected from the host will contain antibodies directed towards the target peptide antigen.

Alternatively, the protein can be used to immunize the host without Adjuvant. In this instance the protein aggregates at body temperature of the host animal (about 37° C.). The heat-induced aggregation increases the immunogenicity of the protein and may fixate the protein in a localized aggregate within the host, generating a heightened immune response and efficient anti-peptide antibody production caused by the induction of macrophage accumulation at the aggregate site and/or the slow release of the antigen from the aggregate.

The antigen-carrier fusion protein can also contain additional peptide sequences to heighten the immune response after administration: For example, B cell- and/or T cell-activating sequences can be added to the protein to increase interaction with the immune system. The fusion protein can also contain sequences which direct immunogenic post-translational modifications (such as heptosylation by the aah enzyme in E. coli) to enhance immunogenicity. Likewise, an affinity tag sequence (such as a $His_6$ tag) can be added to the protein to facilitate purification.

The antigen-carrier fusions can be used to produce polyclonal and monoclonal antibodies for a variety of biomedical and therapeutic applications. In addition these proteins could also be used as protein-based vaccines to immunize humans and animals against a diseases caused by viruses, bacteria, fungi and parasites.

Our invention can be used produce improved peptide antigens by coupling them to antigenic proteins such as GAPDH or GroEL linked to thermally-responsive aggregation peptides such as elastin-like (VPGXG) (SEQ. ID. NO. 4) polymers. However, it is obvious that that one skilled-in-the-art could produce a wide variety of alternative versions of these improved antigens by recombinantly linking carrier proteins to other polypeptide sequences which cause the aggregation of the fusion protein after injection into warm-blooded animals.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of Recombinant Peptide Antigens Fused to Carrier Proteins Containing Thermally-Responsive Aggregation Peptides A peptide antigen (40 residues; protein span Phe 158-Tyr197 from human procaspase-3) was expressed as a fusion protein with the thermally-responsive carrier protein (GroEL protein fused to a 21 kDa TRA polypeptide comprised of VPGVG (SEQ. ID. NO. 2) and VPGFG (SEQ. ID. NO. 3) pentapeptide subunits) using the following procedure. The 120 bp DNA sequence encoding peptide antigen was synthesized and subcloned into the carrier protein expression vectors on the 5' end of the carrier protein open reading frame encoding the E. coli GroEL protein fused at its C-terminus to the thermally-responsive aggregation peptide. The resulting expression plasmid was then transformed into the BL21 STAR E. coli expression strain. These cells were use to inoculate 100 ml bacterial cultures containing rich medium; the cells were grown at 37° C. When the culture density reached an OD 600≈1, the cultures were induced by adding IPTG to the media to a final concentration of 1 mM. After inducing the cultures for 3 hours at 25° C., the cells were harvested by centrifugation and lysed using buffer containing lysozyme and Triton X-100. The resulting peptide antigen-carrier fusion protein was produced at high levels using this procedure.

Example 2

Figure 2:
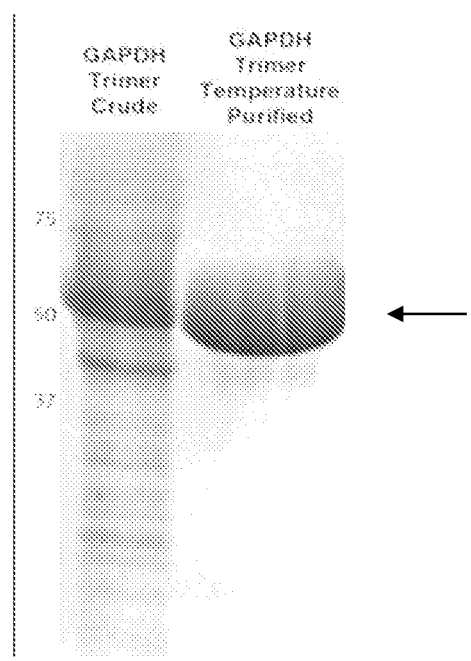
FIG. 2 depicts a gel electrophoresis analysis (SDS-PAGE) of bacterial expression and thermal-cycling purification of carrier-TRA polypeptide fusion protein. The *E. coli* GAPDH protein was fused to the N-terminus of a 21 kDa TRA-polypeptide sequence (the protein also contained a His$_6$ tag sequence to allowed standard column-based purification for reference purposes). The purified protein is indicated by the arrow.

Production and Purification of Immunogenic Carrier Proteins Containing Thermally-Responsive Peptides Thermally-responsive carrier-proteins (such as E. coli GAPDH (glyceraldehyde-3-phosphate dehydrogenase) protein fused to the N-terminus a 21 kDa TRA polypeptide using VPGVG (SEQ. ID. NO. 2) and VPGFG (SEQ. ID. NO. 3) pentapeptide subunits) were produced in bacterial cultures at 25° C. for 3 hours and then the cells were harvested by centrifugation at 4° C. and lysed on ice using a lysozyme/Triton X-100 buffer. After lysis and DNase treatment to reduce viscosity, the samples were centrifuged at 4° C. to remove cell debris. The resulting lysates were heated to 37° C. to precipitate the target protein and the samples were centrifuged at 10,000 rpm for 10 minutes at room temperature. The supernatant was removed from the protein pellet. The protein pellets could be redissolved in cold 1× PBS and then reprecipitated at 37° C. to further purify the proteins (FIG. 2). The protein was >90% pure as measured by SDS-PAGE analysis.

Example 3

Production of Polyclonal Anti-Peptide Antibodies Using Recombinant Peptides Fused to Carrier Proteins Containing Thermally-Responsive Peptides A DNA sequence encoding a peptide antigen from the caspase-3 (csp-3) protein was fused to the 5' terminus of the open reading frame encoding GroEL carrier protein-TRA peptide (14 kDa (dimer) or 21 kDa (trimer) fusions (or GroEL carrier protein lacking TRA peptide as a control). The recombinant antigen-carrier proteins were expressed in bacteria and purified to homogeneity. The peptide antigen-carrier proteins were dialyzed into PBS buffer and, after mixing with Freund's Adjuvant, used to immunize rabbits to produce polyclonal antibodies (0.1 mg protein per rabbit). As a control, rabbits were immunized with the chemically conjugated csp3-KLH control. The rabbits were immunized using a standard protocol (initial immunization with Complete Freund's Adjuvant and 2 injections using Incomplete Freund's Adjuvant then the final 3 injections with protein in 1× PBS). The booster injections were administered every two weeks.

Figure 3:
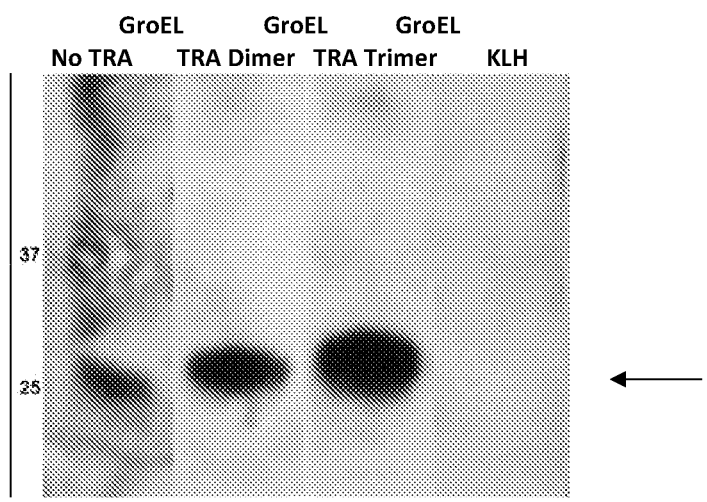
FIG. 3 depicts western blot analysis of caspase-3 zymogen antigen detection using anti-sera produced using csp-3-GroEL-TRA polypeptide proteins. The position of the pro-caspase-3 target antigen is indicated by the arrow. The carriers contained either a 14 kDa (Dimer) or a 21 kDa (Trimer) TRA sequence or no TRA sequence (far left lane of blot). No immunoreactivity was observed for serum produced using csp-3-KLH protein immunogen.

8 weeks after the initial immunization, blood was collected and used to produce sera. The sera were then in phosphate buffered saline and used to perform Western blots using commercially-obtained recombinant procaspase-3. Strong immunoreactivity was observed for the sera produced using the GroEL-TRA carrier (FIG. 3). The peptide GroEL-Trimer (Trimer=21 kDa TRA polypeptide) serum was able to detect 10 ng of protein antigen (commercially-obtained pure recombinant procaspase-3). In this gel system the recombinant procaspase-3 migrates at a molecular weight near 27 kDa. As the size of the TRA domain increased, stronger detection of the procaspase-3 band was observed. Sera produced using csp-3-KLH antigen had difficulty detecting the protein antigen. Strong detection of caspase-3 antigen was also observed in ELISA assays using sera produced using GroEL-TRA carriers.

Example 4

Use of Recombinant Peptides Fused to Carrier Proteins Containing Thermally-Responsive Peptides to Produce Specific Polyclonal Anti-Peptide Antibodies Without Adjuvants We also immunized two rabbits with recombinant csp-3 GAPDH-carrier-TRA protein in 1× PBS only (no Freund's Adjuvant used in any injection). These immunizations (0.1 mg per rabbit) were much faster and easier to perform since we did not have to vortex the sample for 5 minutes to make a stable antigen-adjuvant emulsion prior to injection and the samples passed easily through the syringe needle during each immunization. We also noted that the rabbits appeared to experience less physical discomfort during and after the "PBS-only" injections. Booster injections were administered every two weeks.

Figure 4:
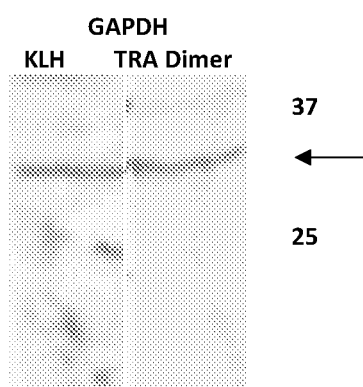
FIG. 4 depicts a western blot analysis of caspase-3 zymogen antigen detection using serum produced without Adjuvant using csp3-GAPDH-TRA immunogen. The serum was used to detect procaspase-3 in Jurkat cell lysates (20 micrograms protein loaded per well). The position of the procaspase-3 is indicated by the arrow. The serum produced using the modified method was compared to serum produced using csp-3 peptide-KLH conjugates using Freund's Adjuvant using the immunization procedure.

8 weeks after the initial immunization, blood was collected and used to produce sera. The sera were then diluted in phosphate-buffered saline and used to perform Western blots to detect procaspase-3 in cellular lysates derived from Jurkat cells. Strong immunoreactivity was observed for the sera produced without Adjuvant (FIG. 4).

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Sequence 1: Amino acid sequence of a recombinant protein immunogen containing a carrier protein (GroEL protein) fused to a thermally-responsive TRA polypeptide (VPGXP) (SEQ ID NO. 4) sequence.

```
MAAKDVKFGNDARVKMLRGVNVLADAVKVTLGPKGRNVVLDKSFGAPTITKDGVSV

AREIELEDKFENMGAQMVKEVASKANDAAGDGTTTATVLAQAIITEGLKAVAAGMNP

MDLKRGIDKAVTAAVEELKALSVPCSDSKAIAQVGTISANSDETVGKLIAEAMDKVGK

EGVITVEDGTGLQDELDVVEGMQFDRGYLSPYFINKPETGAVELESPFILLADKKISNIR

EMLPVLEAVAKAGKPLLIIAEDVEGEALATLVVNTMRGIVKVAAVKAPGFGDRRKAM

LQDIATLTGGTVISEEIGMELEKATLEDLGQAKRVVINKDTTTIIDGVGEEAAIQGRVAQ

IRQQIEEATSDYDREKLQERVAKLAGGVAVIKVGAATEVEMKEKKARVEDALHATRA

AVEEGVVAGGGVALIRVASKLADLRGQNEDQNVGIKVALRAMEAPLRQIVLNCGEEP

SVVANTVKGGDGNYGYNAATEEYGNMIDMGILDPTKVTRSALQYAASVAGLMITTEC

MVTDLPKNDAADLGAAGGMGGMGGMGGMMLEELGPGVGVPGVGVPGLGVPGVGV

PGLGVPGVGVPGLGVPGVGVPGLGVPGVGVPGLGVPGVGVPGLGVPGVGVPGLGVP

GVGVPGLGVPGVGVPGVGVPGLGVPGVGVPGLGVPGVGVPGLGVPGVGVPGLGVPG

VGVPGLGVPGVGVPGLGVPGVGVPGLGVPGVGVPGLGVPGVGVPGVGVPGLGVPGV

GVPGLGVPGVGVPGLGVPGVGVPGLGVPGVGVPGLGVPGVGVPGLGVPGVGVPGLG

VPGVGVPGLGVPGWP
```

What is claimed is:

1. A method of producing an antibody through immunization using a antigen compound, the method comprising:
   obtaining an antigen compound comprising a peptide antigen fused to a carrier protein, wherein the carrier protein is GAPDH, GroEL, or KLH, fused to a thermally-responsive polypeptide sequence containing elastin-like VPGXG (SEQ ID NO. 4) polymers capable of causing the compound to aggregate when heated to temperatures above about 30° C.;
   introducing the antigen compound into a living organism having an internal temperature of greater than 30° C.; and
   collecting antibodies produced by the living organism in response to the antigen compound.

2. The method of claim 1, wherein the antigen compound is introduced into the living organism in the absence of any immunostimulatory adjuvants which enhance the formation of antibodies.

3. The method of claim 1, wherein the peptide antigen has a length of up to about 40 amino acids.

4. The method of claim 1, wherein the carrier protein is GroEL protein fused to a thermally-responsive aggregation polypeptide sequence.

5. The method of claim 1, wherein the carrier protein is GAPDH protein fused to the thermally-responsive aggregation polypeptide sequence.

6. The method of claim 1, wherein the antigen compound further comprises an acceptor sequence which is heptosylated when expressed in an *E. coli* strain expressing the aah (bacterial heptosyl-transferase) enzyme.

7. The method of claim 1, wherein the antigen compound further comprises T cell activating sequences.

8. The method of claim 1, wherein the antigen compound further comprises B cell activating sequences.

9. The method of claim 1, wherein the thermally-responsive polypeptide sequence is capable of causing the compound to aggregate when heated to temperatures above about 37° C.

10. The method of claim 1, wherein the thermally-responsive polypeptide sequence comprises VPGVG (SEQ. ID. NO. 2) and VPGFG (SEQ. ID. NO. 3) pentapeptide subunits.

* * * * *